US012605151B2

(12) United States Patent
Smith et al.

(10) Patent No.: US 12,605,151 B2
(45) Date of Patent: Apr. 21, 2026

(54) MEDICAL SYSTEMS, DEVICES, AND RELATED METHODS

(71) Applicant: Boston Scientific Scimed, Inc., Maple Grove, MN (US)

(72) Inventors: Paul Smith, Smithfield, RI (US); Travis Henchie, Worcester, MA (US); Peter L. Dayton, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 393 days.

(21) Appl. No.: 18/299,161

(22) Filed: Apr. 12, 2023

(65) Prior Publication Data

US 2023/0329687 A1 Oct. 19, 2023

Related U.S. Application Data

(60) Provisional application No. 63/332,023, filed on Apr. 18, 2022.

(51) Int. Cl.
*A61B 17/00* (2006.01)
*A61M 3/02* (2006.01)

(52) U.S. Cl.
CPC .................. *A61B 17/00491* (2013.01); *A61B 2017/0034* (2013.01); *A61M 3/0233* (2013.01)

(58) Field of Classification Search
CPC ...... A61B 17/00491; A61B 217/00292; A61B 217/0034; A61B 17/7097; A61B 17/8805; A61B 17/8822; A61B 17/8833; A61M 31/007
See application file for complete search history.

(56) References Cited

U.S. PATENT DOCUMENTS

| | | | | |
|---|---|---|---|---|
| 2004/0193171 A1* | 9/2004 | DiMauro | ........... | A61B 17/8822 |
| | | | | 606/92 |
| 2004/0260303 A1 | 12/2004 | Carrison | | |
| 2008/0272209 A1* | 11/2008 | Yokoyama | ............ | B05B 7/1281 |
| | | | | 239/10 |
| 2009/0209946 A1* | 8/2009 | Swayze | .............. | A61B 17/3205 |
| | | | | 606/1 |

(Continued)

FOREIGN PATENT DOCUMENTS

| | | |
|---|---|---|
| IT | 202000019642 A1 | 2/2022 |
| WO | 2021059084 A1 | 4/2021 |

OTHER PUBLICATIONS

International Search Report and Written Opinion in PCT/US2023/018242, mailed Jul. 4, 2023 (8 pages).

*Primary Examiner* — Diane D Yabut
*Assistant Examiner* — Christian D Knauss
(74) *Attorney, Agent, or Firm* — Bookoff McAndrews PLLC

(57) ABSTRACT

A medical system includes a medical device having a handle, a shaft, an actuation member, and medical system also includes a cartridge and a plunger. The handle includes an actuator movable relative to the handle, and the actuator is coupled to a distal end of the shaft via the actuation member. The cartridge contains a treatment agent, and the cartridge is couplable to the distal end of the shaft. The plunger is movable relative to the cartridge. Movement of the actuator controls movement of the actuation member. Movement of the actuation member controls movement of either the plunger or the cartridge to control a delivery of the treatment agent from the cartridge.

20 Claims, 6 Drawing Sheets

(56)     References Cited

U.S. PATENT DOCUMENTS

| | | | |
|---|---|---|---|
| 2010/0206905 A1 | 8/2010 | Horner et al. | |
| 2012/0226261 A1* | 9/2012 | Barnett | .................... A61D 1/02 |
| | | | 604/199 |
| 2016/0067406 A1* | 3/2016 | Goodman | ............... A61M 5/19 |
| | | | 604/82 |
| 2018/0071460 A1 | 3/2018 | Rekaya et al. | |
| 2018/0078248 A1 | 3/2018 | Swayze et al. | |
| 2020/0323610 A1 | 10/2020 | Jensrud et al. | |

* cited by examiner

MEDICAL SYSTEMS, DEVICES, AND RELATED METHODS

CROSS-REFERENCE TO RELATED APPLICATIONS

This application claims the benefit of priority under 35 U.S.C. § 119 from U.S. Provisional Application No. 63/332,023, filed Apr. 18, 2022, which is incorporated by reference herein in its entirety.

TECHNICAL FIELD

The present disclosure relates generally to medical systems, devices, and methods. In particular, this disclosure is directed to systems, devices, and methods for delivering one or more agents endoscopically from a distal end of a device.

BACKGROUND

Agents (e.g., treatment agents) may be delivered during medical procedures, such as endoscopic procedures. During an endoscopic procedure, a user inserts a sheath of an endoscope into a body lumen of a patient. The user utilizes a handle of the endoscope to control (e.g., deflect and/or position) the endoscope during the procedure. Tools are passed through a working channel of the endoscope via, e.g., a port in the handle, to deliver treatment at the treatment site near a distal end of the endoscope. The treatment site is internal to the patient, and thus is remote from the user.

During various procedures, agents may be delivered through a device inserted into the working channel of the endoscope. In another aspect, agents may be delivered through the working channel itself, for example, via the port. In either aspect, when the agent is delivered, a portion of the agent may remain within portions of the device or within the working channel, and thus may not be delivered to the procedure site. However, a user may desire to deliver an entirety or near an entirety of an agent, without leaving leftover agent in the device. Additionally, delivering some agents through the length of the device or the working channel may require a force or pressure that may prevent or inhibit a controlled delivery of the agent. Furthermore, many agents (e.g., treatment agents, such as cyanoacrylates or other bonding agents, adhesives, etc.) may cure (i.e., harden) within the device or within the working channel, which may form one or more clogs or obstructions. The clogs or obstructions may prevent or inhibit the delivering of the agent through the device or the working channel. Therefore, a need exists for systems, device, or methods for delivering one or more agents endoscopically.

SUMMARY

According to an example, a medical system may include a medical device having a handle, a shaft, an actuation member, and medical system may also include a cartridge and a plunger. The handle may include an actuator movable relative to the handle, and the actuator may be coupled to a distal end of the shaft via the actuation member. The cartridge may contain a treatment agent, and the cartridge may be couplable to the distal end of the shaft. The plunger may be movable relative to the cartridge. Movement of the actuator may control movement of the actuation member. Movement of the actuation member may control movement of either the plunger or the cartridge to control a delivery of the treatment agent from the cartridge.

The medical system may include one or more of the following features. The treatment agent may be an adhesive. The treatment agent may be a cyanoacrylate. The actuation member may include a sheath extending between the actuator and the plunger, such that distal movement of the actuator urges the sheath and the plunger distally to deliver the treatment agent from the cartridge.

The distal end of the shaft may include a fulcrum element fixed within the distal end of the shaft. The actuation member may include one or more wires that extend from the actuator distally beyond the fulcrum element, and proximally of the fulcrum element to a portion of the plunger, such that proximal movement of the actuator urges the wire proximally and also urges the plunger distally to deliver the treatment agent from the cartridge. The fulcrum element may include a ring fixed within an internal portion of the distal end of the shaft.

The plunger may be fixed to the shaft. The actuation member may include one or more wires that extend from the actuator distally to a proximal portion of the cartridge, such that proximal movement of the actuator urges the one or more wires and the cartridge proximally to deliver the treatment agent from the cartridge. The plunger may be coupled to a distal end of the actuation member. The actuation member may include a threaded portion. The cartridge may include a grooved portion configured to interface with the threaded portion of the actuation member, such that rotation of the actuation member advances the plunger within the cartridge.

The cartridge may be removably coupled to the distal end of the shaft. The cartridge may include a proximal extension with a peg. The distal end of the shaft may include a slot, and positioning the proximal extension within the slot may removably couple the cartridge to the distal end of the shaft. The slot may include a longitudinal slot and a radial slot. The radial slot may extend along a portion of an inner circumferential surface of the shaft in a direction perpendicular to a longitudinal axis of the shaft.

The handle may include a plurality of markings indicative of an amount of the treatment agent that has been delivered and/or remains within the cartridge. The cartridge may include a distal cover that is either openable or removable to expose a distal opening of the cartridge and to allow the treatment agent to be delivered from the distal opening. The distal cover may be a plug, and the plug may be coupled to the cartridge via a connecting element. The medical system may further include a liner element. The liner element may be coupled to a distal end of the cartridge, and the liner element may be hydrophobic and/or non-stick.

In another example, a medical device may include a cartridge and a plunger. The cartridge may contain a treatment agent. The cartridge may include a proximal extension with a peg, and the cartridge may removably couplable to a distal end of a shaft via the proximal extension. The plunger may be movable relative to the cartridge. Movement of the plunger or the cartridge may control a delivery of the treatment agent from the cartridge.

The medical device may include one or more of the following features. The treatment agent may be a cyanoacrylate. The cartridge may include a distal cover that is removable or openable to expose a distal opening of the cartridge and to allow the treatment agent to be delivered from the distal opening.

In yet another example, a method may include delivering a distal end of a medical device to a treatment site, manipulating an actuator on a proximal handle to deliver an agent from a cartridge to the treatment site, and removing the medical device and the cartridge from the treatment site. The actuator may actuate a non-fluidic actuation member to control movement of a plunger or the cartridge.

The method may include one or more of the following features. The method may further include attaching the cartridge to the distal end of the medical device. Furthermore, the method may include, before manipulating the actuator on the proximal handle to deliver the agent from the cartridge to the treatment site, opening or exposing a sealed distal end of the cartridge. Moreover, the method may further include after removing the medical device and the cartridge from the treatment site, uncoupling the cartridge from the distal end of the medical device, and coupling another cartridge to the distal end of the medical device.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate examples of the present disclosure and together with the description, serve to explain the principles of the disclosure.

DETAILED DESCRIPTION

Figure 1:
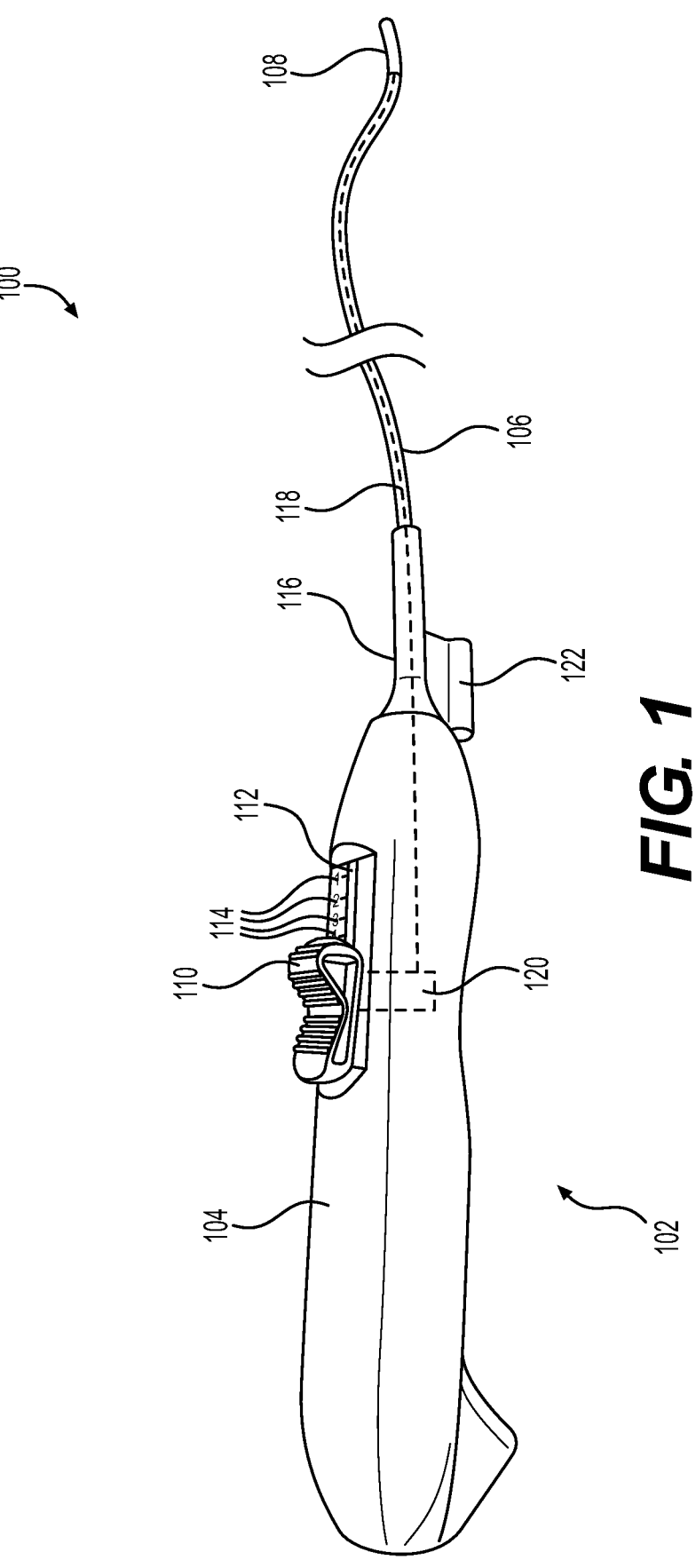
FIG. 1 illustrates a perspective view of an exemplary medical system, including a medical device with a handle portion and an insertion portion, and a cartridge at a distal end of the insertion portion, according to aspects of this disclosure.

The terms "proximal" and "distal" are used herein to refer to the relative positions of the components of an exemplary medical system and exemplary medical devices. When used herein, "proximal" refers to a position relatively closer to the exterior of the body or closer to a medical professional using the medical system or medical device. In contrast, "distal" refers to a position relatively further away from the medical professional using the medical system or medical device, or closer to the interior of the body. As used herein, the terms "comprises," "comprising," "having," "including," or other variations thereof, are intended to cover a non-exclusive inclusion, such that a system, device, or method that comprises a list of elements does not include only those elements, but may include other elements not expressly listed or inherent thereto. Unless stated otherwise, the term "exemplary" is used in the sense of "example" rather than "ideal." As used herein, the terms "about," "substantially," and "approximately," indicate a range of values within +/−10% of a stated value.

Examples of this disclosure include systems, devices, and methods for facilitating and/or improving the efficacy, efficiency, cost, and/or safety of a medical procedure. Embodiments of the disclosure may relate to systems, devices, and methods for performing various medical procedures and/or treating portions of anatomy, for example, accessed via a body lumen, such as the larynx, trachea, bronchi (primary bronchi), lobar (secondary bronchi), segmental (tertiary bronchi), bronchiole, terminal bronchiole, or any other portion of the respiratory system. Additionally, embodiments of the disclosure may relate to systems, devices, and methods for performing various medical procedures and/or treating portions of the large intestine (colon), small intestine, cecum, esophagus, stomach, or any other portion of the gastrointestinal tract or biliary tree. Furthermore, embodiments of the disclosure may relate to systems, device, and methods for performing various medical procedures and/or treating portions of the kidneys, ureters, bladder, urethra, or any other portion of the urinary tract. In these aspects, the systems, devices, and methods discussed herein may be used to treat any other suitable patient anatomy (collectively referred to herein as a "treatment site").

Various embodiments described herein include single-use or disposable medical devices. Some aspects of the disclosure may be used in performing an endoscopic, arthroscopic, bronchoscopic, ureteroscopic, colonoscopic, or other type of procedure. For example, the disclosed aspects may be used with duodenoscopes, endoscopes, gastroscopes, endoscopic ultrasonography ("EUS") scopes, colonoscopes, ureteroscopes, bronchoscopes, laparoscopes, arthroscopes, cytoscopes, aspiration scopes, sheaths, catheters, diagnostic or therapeutic tools or devices, or any other suitable delivery device or medical device, for example, for treatment through a body lumen. Alternatively, various embodiments described herein may be delivered to a treatment site alone and/or used separate from another scope or medical device. One or more of the elements discussed herein could be metallic, plastic, or include a shape memory metal (such as Nitinol), a shape memory polymer, a polymer, or any combination of biocompatible materials.

Reference will now be made in detail to examples of the disclosure described above and illustrated in the accompanying drawings. Wherever possible, the same reference numbers will be used throughout the drawings to refer to the same or like parts. It is noted that one or more aspects of the medical systems, devices, and methods discussed herein may be combined and/or used with one or more aspects of other medical systems, devices, and methods discussed herein.

FIG. 1 depicts a medical system ("system") 100. System 100 includes a medical device 102, including a handle portion ("handle") 104 and a shaft/insertion portion ("shaft") 106. Medical device 102 may be referred to herein as an endoscope, but it should be appreciated that medical device 102 may be an endoscope, duodenoscope, bronchoscope, ureteroscope, colonoscope, catheter, or other type of medical device. Additionally, system 100 includes a cartridge 108, which may be integrally formed with shaft 106 (i.e., at a distal end of shaft 106), or may be coupled (e.g., releasably coupled) to a distal portion of shaft 106. As discussed in detail below, cartridge 108 may contain one or more agents (e.g., fluidic adhesives or other treatment agents), and action on handle 104 may control the delivery of the one or more agents, for example, via a non-fluidic actuation member that extends from handle 104 and through at least a portion of shaft 106.

In these aspects, the non-fluidic actuation member may help to allow for a controlled (e.g., gradual, measured, and/or more precise) delivery or administration of one or more agents, for example, for treatment at one or more locations accessed via a body lumen. The non-fluidic actuation member may help to provide the user with the ability to control the start of the delivery of the fluidic agent, and/or also to stop (e.g., pause or end) the delivery of the fluidic agent. In some aspects, the non-fluidic actuation member may allow the user to exert pressure or apply a force on a fluidic agent, without the user having to rely on a barrel strength, rigidity, etc. of shaft 106. Additionally, the non-fluidic actuation member may allow for multiple cartridges (i.e., different cartridges) to be coupled to the distal end of shaft 106. Furthermore, the non-fluidic actuation member may flex, bend, deflect, etc. as the distal end of shaft 106 is delivered to the treatment site. Although not shown, one or more portions of system 100 (e.g., shaft 106 and cartridge 108) may be delivered to the treatment site through or along one or more portions of an insertion device (e.g., a sheath, scope, etc.). Alternatively, one or more portions of system 100 (e.g., shaft 106 and cartridge 108) may otherwise be delivered to the treatment site. Furthermore, in some aspects, aspects discussed herein may allow delivery of a fluidic agent, while having a small footprint (i.e., a small cross-sectional shape) to be delivered to the treatment site, either via an insertion device (i.e., within a small channel or lumen in the insertion device or adjacent to an outer wall of the insertion device, i.e., in a "side-saddle" arrangement) or alone.

As mentioned, medical device 102 includes handle 104 and shaft 106. Handle 104 includes at least one actuator 110. As discussed below, actuator 110 may be moveable within a slot 112, for example, to help control the delivery of the one or more agents from cartridge 108. Additionally, a portion of handle 104, for example, a portion of handle 104 adjacent to slot 112, may include one or more indications, graduations, or markings 114, for example, along at least a portion of slot 112. Markings 114 may help to indicate the position of actuator 110 within slot 112 to the user. In this aspect, handle 104 may include four markings 114, such as, for example, numbers, indications, graduations or other markings corresponding to an amount (e.g., volume) of the one or more agents remaining in cartridge 108 based on the position of actuator 110 within slot 112 and/or an amount (e.g., volume) of the one or more agents delivered from cartridge 108. It is noted that handle 104 may include any number of markings 114 to help correlate an amount of the one or more agents in cartridge 108 to a position of actuator 110. In some examples, markings 114 (i.e., in the form of graduations) may form a ratchet or other component to help provide haptic or tactile feedback to the user controlling actuator 110. For example, actuator 110 may be movable between stops or clicks in slot 112, which may help correlate the amount of the one or more agents delivered from cartridge 108. Alternatively or additionally, markings 114 may provide visual feedback to the user controlling actuator 110. Furthermore, although FIG. 1 illustrates actuator 110 being a slider, it will be appreciated that any suitable actuator(s) may be used in addition to or in place of actuator 110, such as one or more levers, buttons, knobs, joysticks, etc.

Shaft 106 may extend from a distal end of handle 104. A shaft strain relief portion 116 may help couple shaft 106 to handle 104, for example, such that shaft may deflect or articulate relative to handle 104. Furthermore, although not shown, handle 104 may include one or more of a deflection or articulation lever, a suction port, an instrument or irrigation port, etc.

As discussed below and as shown in greater detail in FIGS. 2A-2C, 3A, 3C, 5A, and 5B, one or more actuation members 118 (e.g., a wire, a cable (e.g., a Bowden cable), a strand, a cord, a chain, a thread, etc.) may extend from handle 104 and through a portion of shaft 106 (e.g., through an internal lumen of shaft 106). For example, actuation member 118 may be coupled to actuator 110 via an actuator extension 120. For example, actuator extension 120 may extend from actuator 110 into an internal portion of handle 104. Actuator extension 120 may be movable (e.g., longitudinally movable) within an internal portion of handle 104, for example, based on movement of actuator 110 to control movement (i.e., distally or proximally) of actuation member 118.

Medical device 102 may also include a cleaning portion or a cleaning tool 122. Cleaning tool 122 may extend from a distal portion of handle 104, for example, adjacent to and/or parallel to a proximal portion of shaft 106. Cleaning tool 122 may include a cylindrical housing surrounding a pin or other elongate member (not shown). As discussed below, cleaning tool 122 may be used to help clean one or more portions of cartridge 108 (e.g., a distal opening). For example, cleaning tool 122 may include one or more of the aspects shown and discussed in U.S. application Ser. No. 16/834,003, published as U.S. Pre-Grant Publication No. 2020/0323610, which is incorporated herein by reference.

As discussed below, cartridge 108 may be releasably coupled to a distal end of shaft 106. Then, a portion of medical device 102 (i.e., shaft 106) may be delivered though or along an exterior of an insertion device to a treatment site, or may be separately delivered to the treatment site. Alternatively or additionally, various aspects of medical device 102 (e.g., actuator 110 and actuation member 118) may be integrated into an insertion device handle and/or an insertion device shaft, and the insertion device shaft may be delivered to the treatment site. In these aspects, an endoscope may include one or more controls or actuators for controlling and/or actuating cartridge 108.

Figure 2C:
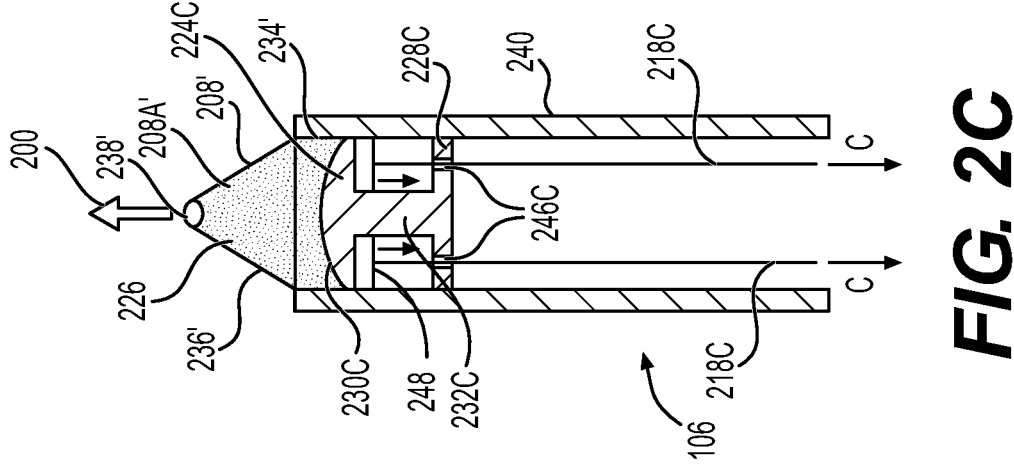
FIG. 2A-2C are cross-sectional views of various embodiments of the distal end of the insertion portion and the cartridge, according to aspects of this disclosure.
Figure 2B:
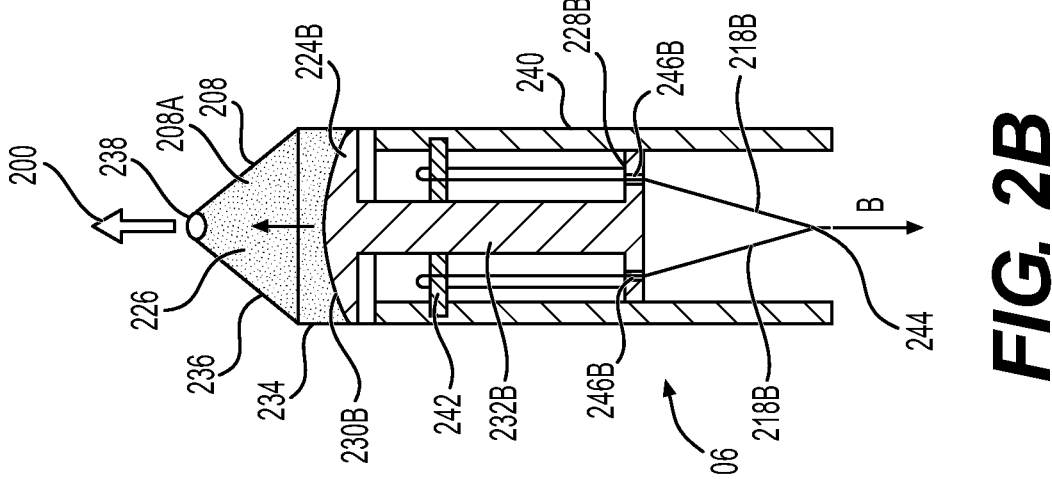
Figure 2A:
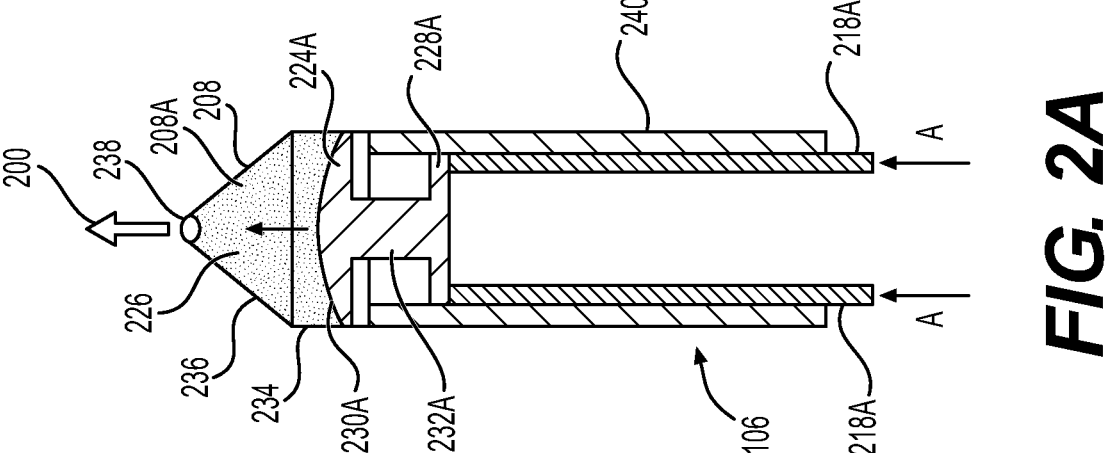

FIGS. 2A-2C are cross-sectional views of different embodiments of actuation members within a portion of shaft 106 and interacting with cartridges 208, 208'. Movement of actuator 110 (FIG. 1) may control the movement of one or more actuation members 218A, 218B, 218C, and thus control relative movement of a plunger 224A-224C and/or cartridge 208, 208' to help deliver one or more agents 226 from cartridge 208, 208', for example, from within an interior cartridge cavity 208A. As shown in FIGS. 2A-2C, each plunger 224A-224C may include a proximal portion 228A-228C, respectively, which may abut one or more actuation members. Each plunger 224A-224C may also include a distal portion 230A-230C, for example, connected to respective proximal portion 228A-228C via a respective elongate portion 232A-232C. Distal portions 232A-232C may include a dome-shaped distal end. Alternatively, distal portions 232A-232C may include a different shaped distal end, for example, a flat distal end, a conical distal end, a shape that tapers in size in a distal direction, etc. Each plunger 224A-224C may be coupled to or be a part of shaft 106. Alternatively, plunger 224A-224C may be coupled to or a part of cartridge 208, 208'.

In some examples, one or more portions of shaft 106 may include an outer diameter sized or otherwise configured to fit within a working channel of an endoscope, for example, within an endoscope working channel with a diameter of approximately 2.8 mm to approximately 6.0 mm. Alternatively, as mentioned above, one or more portions of shaft 106 may be delivered to a treatment site along or adjacent to an outer circumference of a delivery portion of an endoscope, for example, in a side-saddle arrangement. Furthermore, in some examples, one or more portions of cartridge 208, 208' may be sized, shaped (e.g., angles, curvatures, etc.), or otherwise configured to correspond to an interior portion of shaft 106. Additionally, in some examples, one or more portions of plunger 224A-224C may be sized, shaped (e.g., angles, curvatures, etc.), or otherwise configured to correspond to an interior portion of cartridge 208, 208'. One or more components discussed herein may be formed of a non-stick, lubricous material. One or more components may be formed of, for example, one or more of polytetrafluoroethylene (PTFE), expanded polytetrafluoroethylene (EPTFE), fluorinated ethylene propylene (FEP), an acetyl plastic such as, for example, polyoxymethylene (POM), Delrin®, Delron, polyethylene (PE), nylon, or other appropriate material As mentioned above, cartridge 208 may contain a supply of one or more agents 226. Agent 226 may be a treatment agent, such as a cyanoacrylate or other bonding agent, adhesive, etc. In other aspects, agent 226 may include one or more of an antimicrobial agent (e.g., one or more antibacterial agents), an anticoagulation agent, a coagulating agent, etc. Alternatively or additionally, agent 226 may include one or more a chemotherapy agent, a contrasting agent (e.g., a bulking agent dye for marking one or more anatomies), a dye for a visualization enhancer (e.g., indigo carmine, iodine based solutions, such as, for example, Lugol's solution, a vital dye, etc.), or other agent to be delivered in a targeted and/or controlled manner. Additionally, in some aspects, cartridge 208, 208' may contain a number of agents, for example, mixed, layered or separated in different portions of cartridge 208, etc. For example, in one or more aspects, cartridge 208 may include a first agent in a distal section of cartridge 208, and a second agent different from the first agent in a proximal section of cartridge 208.

As shown in FIGS. 2A-2C, cartridge 208 may include a proximal portion 234, for example, which may be substantially cylindrical and may be positioned within or adjacent to a distal end of shaft 106. Cartridge 208 may also include a distal portion 236, which may extend from proximal portion 234 and may include a partially conical shape, or a shape that tapers in size in a distal direction. Cartridge 208 may also include a distal opening 238. Distal opening 238 may be a circular opening, or may be a slit, frangible section, etc. in order for an agent to be delivered from cartridge 208, for example, via movement of distal portion 230A, 230B of plunger 224A, 224B within cartridge 208. As shown in FIG. 2C, a cartridge 208' may be positioned within a distal portion of shaft 106, for example, a proximal portion 234' and/or a distal portion 236' may have smaller lateral cross-sectional areas than proximal portion 234 and distal portion 236 of cartridge 208 (FIGS. 2A and 2B). A distal opening 238' of cartridge 208' may be the same size or a different size than distal opening 238. Additionally, relative movement of plunger 224C and cartridge 208' may control the delivery of one or more agents 226 from cartridge 208'.

FIG. 2A is a first embodiment of shaft 106 and cartridge 208. As shown, shaft 106 includes a sheath, for example, an outer sheath 240. Outer sheath 240 may enclose an actuation member 218A, which may be an inner sheath. In these aspects, actuation member 218A may be movable (e.g., longitudinally) relative to and within outer sheath 240. The inner sheath that forms actuation member 218A may abut outer sheath 240. Actuation member 218A may abut proximal portion 228A of plunger 224A, for example, at a circular interface around a perimeter of proximal portion 228A. As shown, actuation member 218A may have an internal lumen, and may flex, bend, deflect, etc. as shaft 106 is delivered to the treatment site. Alternatively, actuation member 218A may be a solid member, for example, a solid cylindrical member. A proximal portion of actuation member 218A may be coupled to actuator 110 (FIG. 1), either directly or via one or more intermediate elements, and thus may form an actuation member. Although not shown, a separate actuation member may extend from actuator 110 (FIG. 1), and the separate actuation member may be coupled to the sheath-like actuation member 218A. A distal end of actuation member 218A may abut and/or be coupled to proximal portion 228A of plunger 224A.

In one or more aspects, distal end of actuation member 218A may be coupled to proximal portion 228A of plunger 224A, for example, via an adhesive, a snap-fit, a press-fit, or other coupling. As shown in FIG. 2A, distal movement (i.e., in direction A) of actuation member 218A, for example, via distal movement of actuator 110 (FIG. 1), may urge plunger 224A distally. Distal movement of plunger 224A within a portion of cartridge 208, 208' may urge agent(s) 226 distally out of distal opening 238 of cartridge 208, 208' to the treatment site, for example, in direction 200. Additionally, the position of plunger 224A within cartridge 208, 208' corresponds to the position of actuator 110 in slot 112 (FIG. 1), so the user may be able to determine an amount of agent 226 already delivered to the treatment site and/or an amount of agent 226 remaining in cartridge 208, 208'. As mentioned and as shown in FIG. 1, handle 104 may include one or more indications or markings, for example, along at least a portion of slot 112, for example, to indicate the position of actuator 110 within slot 112 to the user, and thus the position of plunger 224A within cartridge 208, 208'.

FIG. 2B illustrates another embodiment of a distal end of shaft 106 and cartridge 208. As shown, shaft 106 includes outer sheath 240. Additionally, an actuation member 218B (e.g., a wire, a cable (e.g., a Bowden cable), a strand, a cord, a chain, a thread, etc.) may be positioned within outer sheath 240. A proximal portion of actuation member 218B may be coupled to actuator 110 (FIG. 1), either directly or via one or more intermediate elements. A fixation element or fulcrum element 242, for example, an at least partially circular element or ring, may be positioned within a distal end of shaft 106, for example, within distal ends of outer sheath 240. Alternatively, fulcrum element 242 may include one or more loops, hooks, ledges, etc. that extend radially inward within the distal end of outer sheath 240, for example, to movably received portions of actuation member 218B. Additionally, a plunger 224B includes proximal portion 228B, distal portion 230B, and elongate portion 232B. Fulcrum element 242 may be positioned between proximal portion 228B and distal portion 230B of plunger 224B, for example, adjacent to a portion of elongate portion 232B.

Actuation member 218B may extend distally from actuator 110 within outer sheath 240, and may extend distally through or around fulcrum element 242. Actuation member 218B may then form a loop and extend proximally back and be coupled to proximal portion 228B of plunger 224B. Actuation member 218B is movable relative to fulcrum element 242, for example, via movement of actuator 110 (FIG. 1). As shown in FIG. 2B, proximal movement (i.e., in direction B) of actuation member 218B, for example, via proximal movement of actuator 110, may urge plunger 224B distally. For example, because actuation member 218B loops around fulcrum element 242, and is then connected to proximal portion 228B of plunger 224B, proximal movement of actuator 110 pulls proximal portion 228B distally to urge plunger 224B distally.

As shown in FIG. 2B, actuation member 218B may include a bisection or split 244. In this aspect, actuation member 218B may include two portions extending distally from split 244. Actuation member 218B may loop around two portions of fulcrum element 242, and may be coupled to two portions of proximal portion 228B of plunger 224B. As such, actuation member 218B may apply force to plunger 224B at two locations, for example, to evenly urge plunger 224B distally. Moreover, proximal portion 228B of plunger 224B may include one or more slots 246B, for example, to movably receive respective portions of actuation member 218B that extend distally to loop around fulcrum element 242. It is noted that the initial position of actuator 110 in this embodiment may be in a distal portion of slot 112 (FIG. 1). As discussed above, distal movement of plunger 224B (resulting from proximal movement of actuation member 218B) within a portion of cartridge 208 may urge agent(s) 226 within cartridge cavity 208A distally out of distal opening 238 of cartridge 208 to the treatment site, for example, in direction 200.

FIG. 2C illustrates another embodiment of a distal end of shaft 106 and cartridge 208', which may at least partially be positioned within a distal portion of shaft 106, as mentioned above. As shown, shaft 106 includes outer sheath 240. Additionally, one or more actuation members 218C (e.g., a wire, a cable (e.g., a Bowden cable), a strand, a cord, a chain, a thread, etc.) may be positioned within outer sheath 240. For example, the one or more actuation members 218C may include two actuation members 218C. A proximal portion of actuation member(s) 218C may be coupled to actuator 110 (FIG. 1), either directly or via one or more intermediate elements. Additionally, a plunger 224C, which includes proximal portion 228C, distal portion 230C, and elongate portion 232C, may be positioned within a distal portion of shaft 106. Plunger 224C may be fixed relative to a distal portion of shaft 106, for example, within a distal portion of outer sheath 240. Plunger 224C may be fixed within the distal portion of shaft 106 via an adhesive, a snap-fit, a press-fit, or other coupling. Cartridge 208' may be coupled to actuation member(s) 218C, such that cartridge 208' may be movable relative to plunger 224C and shaft 106. For example, actuation member 218C may include two actuation members 218C coupled to respective sides of a proximal end 248 of cartridge 208'. Moreover, proximal portion 228C of plunger 224C may include one or more slots 246C, for example, to movably receive respective portions of actuation members 218C, such that actuation members 218C may move relative to proximal portion 228C. Additionally, the position of the two actuation members 218C apply force to cartridge 208' at two locations, for example, to evenly urge cartridge 208' proximally.

Actuation member(s) 218C may extend distally from actuator 110 (FIG. 1) within outer sheath 240, and may extend to proximal end 248 of cartridge 208'. Actuation member 218C may be coupled to proximal end 248 via an adhesive, a snap-fit, a press-fit, or other coupling. As shown in FIG. 2C, proximal movement (i.e., in direction C) of actuation members 218C, for example, via proximal movement of actuator 110 (FIG. 1), may urge cartridge 208' proximally. It is noted that the initial position of actuator 110 in this embodiment may be in a distal portion of slot 112

(FIG. 1). In this aspect, proximal movement of cartridge 208' relative to plunger 224C may cause distal portion 230C of plunger 224C to exert a force on agent(s) 226, thereby urging agent(s) 226 within a cartridge cavity 208A' distally out of distal opening 238' of cartridge 208' to the treatment site, for example, in direction 200.

In these aspects, one or more non-fluidic elements (e.g., actuation members 218A-218C) may actuate and help to control the delivery of a fluidic agent (e.g., agent(s) 226) to the treatment site. Alternatively, although not shown, cartridge 208, 20A and/or plunger(s) 224A-224C may be actuated by a fluidic flow. For example, an actuation member may be a flow of air or fluid, for example, to actuate and/or move a plunger relative to a cartridge (or to actuate and/or move a cartridge relative to a plunger) to deliver one or more agents 226 from the cartridge.

Figures 3A, 3B, 3C:
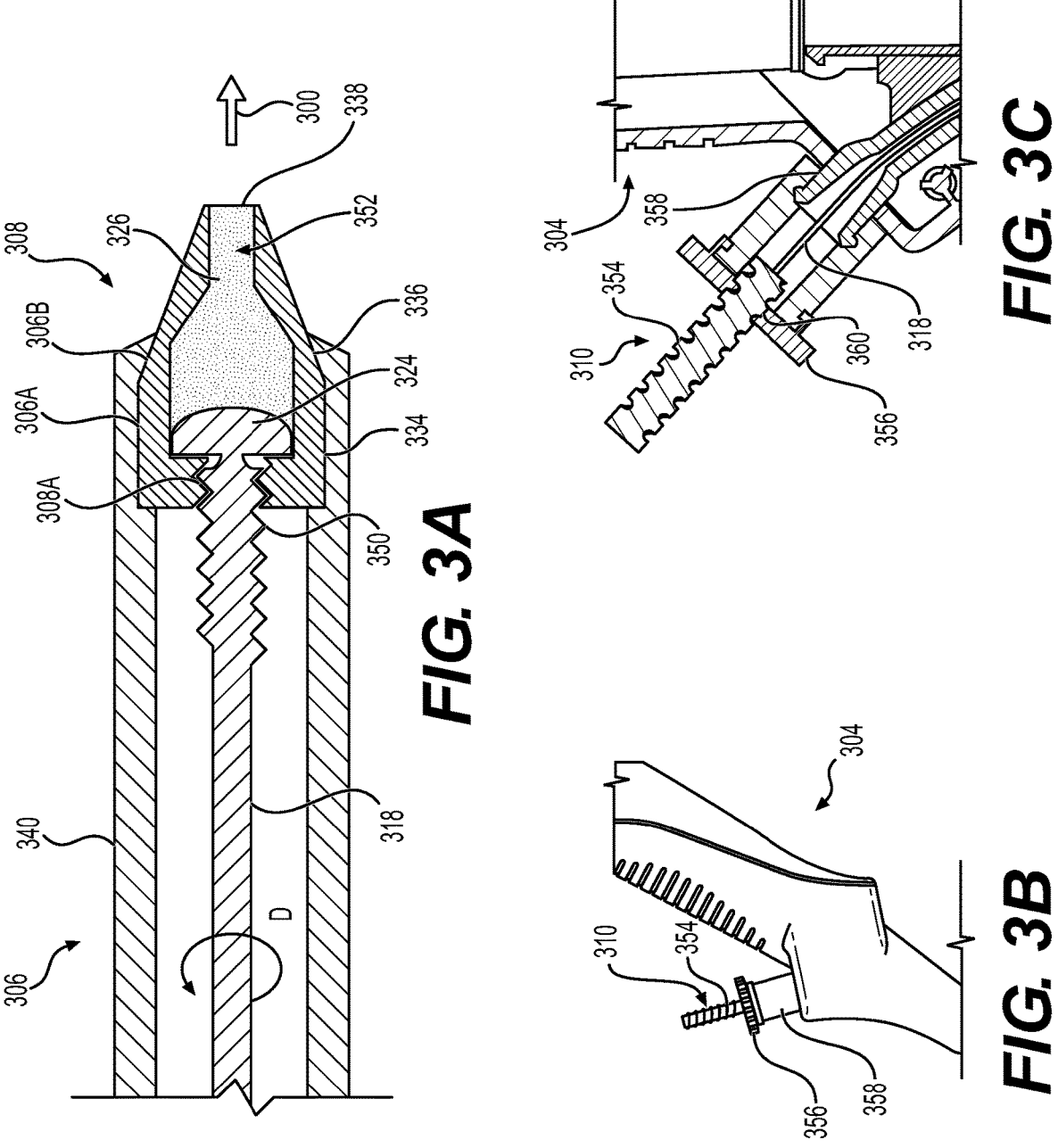
FIG. 3A is a cross-sectional view of another embodiment of the distal end of the insertion portion and an exemplary cartridge.
FIGS. 3B and 3C are side and cross-sectional views of the handle and an actuator coupled to the handle, according to additional aspects of this disclosure.

FIGS. 3A-3C illustrate additional aspects of a handle 304 (FIGS. 3B and 3C), a shaft 306 (FIG. 3A), and a cartridge 308 (FIG. 3A). As shown in FIG. 3A, actuation member 318 includes a plunger portion 324. Additionally, actuation member 318 may be rotatable (e.g., in direction D), for example, via action on an actuator 310 on handle 304 (FIGS. 3B and 3C). At least a distal portion of actuation member 318 includes a threaded portion 350. Additionally, cartridge 308 may include a grooved (or female threaded) portion 308A, for example, to rotatably receive a portion of threaded portion 324. Alternatively, although not shown, a distal portion of shaft 306 may include a threaded portion configured to rotatably receive threaded portion 350. In these aspects, rotating actuation member 318 (via rotation of actuator 310) in a first direction (i.e., direction D) may advance actuation member 318 and plunger portion 324 relative to cartridge 308, for example, to push agent 326 distally out of a distal opening 338 of cartridge 308, for example, in direction 300. Conversely, rotating actuation member 318 in a second direction (i.e., opposite to direction D) may retract actuation member 328 and plunger portion 324 relative to cartridge 308.

Additionally, as shown, shaft 306 may include a sheath 340. An inner surface of sheath 340 may include an indented or reduced thickness portion 306A, for example, at a distal end of shaft 306 to accommodate a portion of cartridge 308. For example, proximal portion 334 of cartridge 308 may be received within a distal portion of shaft 306 in indented portion 306A. Furthermore, an inner surface of shaft 306 may include an angled portion 306B at a distalmost end, for example, to overlap with a portion of a distal portion 336 of cartridge 308. In these aspects, cartridge 308 may be coupled to shaft 306 (e.g., to a distal portion of sheath 340) via an adhesive, a snap-fit, a press-fit, or other coupling.

Distal portion 336 of cartridge 308 may include an internal taper, for example, including a reduced internal cross-section. Additionally, an internal portion of cartridge 308 may include a distal lumen 352. In this aspect, the internal taper of distal portion 336 and/or distal lumen 352 may form one or more stop surfaces to limit the distal movement of plunger portion 324. Although not shown, distal portions of shaft 106 of the embodiments of FIGS. 2A-2C may also include indented portion 306A and/or angled portion 306B, for example, to help accommodate and/or retain cartridges.

FIGS. 3B and 3C illustrate details of handle 304, including actuator 310. FIG. 3B is a side view of a portion of handle 304, and FIG. 3C is a lateral cross-sectional view of a portion of handle 304. As discussed above, handle 304 may be coupled to shaft 306 (FIG. 3A). Actuator 310 may be movable relative to a portion of handle 304. In these aspects, actuator 310 may be coupled to actuation member 318 (FIG. 3C).

As shown in FIGS. 3B and 3C, actuator 310 may include a screw 354, for example, including a cylindrical body with a spiral threading. A proximal portion of screw 354 may extend from handle 304, and a distal portion of screw 354 may be coupled to a proximal end of actuation member 318. Alternatively, screw 354 and actuation member 318 may be a single unitary component. Furthermore, in another aspect, screw 354 and actuation member 318 may be indirectly coupled via one or more intermediary elements. Additionally, in some aspects, screw 354 may be coupled to handle 304 via a coupler 356. Coupler 356 may be coupled to (e.g., fixedly or temporarily mounted on) a portion of handle 304, for example to an instrument port 358. Coupler 356 may include an internal threading, for example, corresponding to the threading on screw 354. In this aspect, screw 354 and coupler 356 may form an interface 360 such that rotation of screw 354 relative to coupler 356 advances or retracts screw 354. Additionally or alternatively, although not shown, actuator 310 may include a dial, a wheel, or another user interface configured to convey rotation to actuation member 318.

In these aspects, rotating screw 354 relative to coupler 356 may advance or retract screw 354 relative to handle 304, and thus distally extend and/or proximally retract actuation member 310, while also rotating actuation member 310 (e.g., in direction D, as shown in FIG. 3A). Furthermore, the size and/or spacing of the threading on screw 354 and/or coupler 356 may correspond to an amount (e.g., volume) of agent 326 within cartridge 308. For example, in this aspect, rotating screw 354 a certain amount (e.g., a quarter rotation, a half rotation, one rotation, etc.) to advance or retract screw 354 may advance or retract actuation member 310, and thus plunger portion 324, by a certain distance. In one example, rotating screw 354 a half rotation may deliver a quarter of the volume of agent 326 within cartridge 308. Furthermore, screw 354, coupler 356, or one or more portions of handle 304 may include one or more indications (not shown) such that the position of screw 354 relative to coupler 356 and/or handle 304 may indicate the amount of agent 326 within cartridge 308 and/or the amount of agent 326 delivered from cartridge 308.

In some aspects, although not shown, cartridge 308 may be removable from sheath 340 with plunger portion 324 (or a portion of plunger portion 324) remaining in and/or coupled to cartridge 308. For example, actuation member 318 may be selectively mated (i.e., coupled and uncoupled) to plunger portion 324. In this aspect, actuation member 318 may mate with plunger portion 324 when cartridge 308 is coupled to the distal portion of sheath 340, and actuation member 318 may disconnect from plunger portion 324 when cartridge 308 is uncoupled from the distal portion of sheath 340. Alternatively or additionally, plunger portion 324 may be a part of cartridge 308 (e.g., a non-removable part of cartridge 308). For example, a distal portion of actuation member 318 may abut a proximal portion of plunger portion 324, such that distal movement (with or without rotation) of actuation member 318 may also distally advance plunger portion 324, without actuation member 318 and plunger portion 324 being solidly coupled or attached.

FIGS. 4A-4E are side views of distal end of a shaft 406 and cartridges 408A-408E with various distal covers 462A-462E at a distal end of cartridges 408A-408E, respectively. Distal covers 462A-462E may help to form a seal at the distal end of cartridges 408A-408E. The seals may help to form a closed end at the distal end of cartridges 408A-408E, for example, during the delivery of shaft 406 and cartridges 408A-408E to the treatment site and/or before the delivery of the agent(s). The closed end at the distal end of cartridges 408A-408E may help to protect the agent(s) stored within cartridges 408A-408E from inadvertent delivery and/or from inadvertent contact with fluid(s) or exposure at or near the treatment site. Then, the seals formed by distal covers 462A-462E may be opened, for example, pushed, pierced, or otherwise opened. For example, as discussed above, relative movement of the plunger and cartridge may push the agent within the cartridge distally, and the agent may abut and push distal covers 462A-462E to open the seals. Moreover, distal covers 462A-462E may be couplable to respective distal ends of cartridges 408A-408E. Alternatively, distal covers 462A-462E may be integrally formed with or on distal ends of cartridges 408A-408E.

Figure 4A:
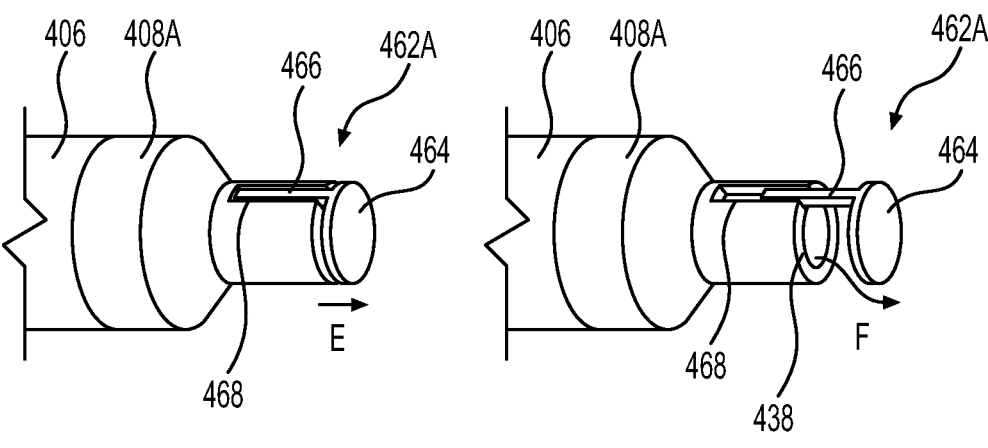
FIGS. 4A-4E are side views of the distal end of the insertion portion and the cartridge with various exemplary distal covers at a distal end of the cartridge, according to various aspects of this disclosure.

FIG. 4A shows shaft 406, cartridge 408A, and a first distal cover 462A in a first, closed configuration (left) and a second, open configuration (right). First distal cover 462A may be a movable cap or pressure valve. For example, distal cover 462A may include an end cap 464 and an extension 466. End cap 464 may cover at least a portion of distal opening 438 of cartridge 408A. Cartridge 408A may include a channel 468, for example, extending longitudinally in a distal portion of cartridge 408A, for example, extending proximally from distal opening 438. Extension 466 may extend into and be movable (e.g., longitudinally movable) within channel 468 to extend and/or retract distal cover 462A, and may help maintain a connection between end cap 464 and cartridge 408A. For example, distal cover 462A may be movable in direction E to at least partially expose distal opening 438, such that the one or more treatment agents in cartridge 408A may be delivered, for example, in direction F. First distal cover 462A, including end cap 464 and/or extension 466, may be urged in direction E by the force of the agent within cartridge 408A, and/or may be urged in direction E by other user actuation, as discussed with respect to FIG. 5B below. Although not shown, distal cover 462A may include a biasing element, for example, a spring connected to a proximal portion of extension 466. In this aspect, when the plunger (not shown) and/or cartridge 408A are stationary and some or all of the agent(s) has been delivered from cartridge 408A, distal cover 462A may help to close distal opening 438.

Figure 4B:
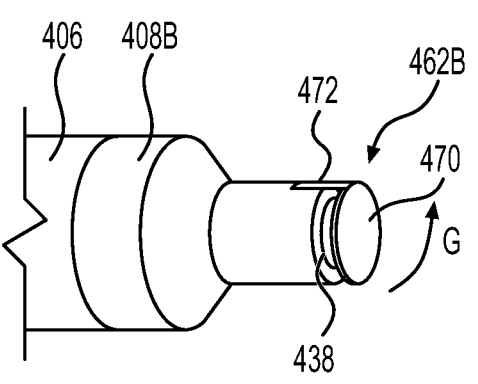

FIG. 4B shows shaft 406, cartridge 408B, and a second distal cover 462B. FIG. 4B illustrates second distal cover 462B in a partially open configuration. Although not shown, second distal cover 462B may abut distal opening 438 in a closed configuration. Second distal cover 462B may be a movable flap. For example, distal cover 462B may include an end flap 470 and an arm 472. End flap 470 may cover at least a portion of distal opening 438 of cartridge 408B. Arm 472 may be coupled to a distal portion of cartridge 408B. Additionally, end flap 470 and/or arm 472 may be pivotable, for example, in direction G to at least partially expose distal opening 438, such that the one or more agents in cartridge 408B may be delivered. Second distal cover 462B, including end flap 470 and/or arm 472, may be urged in direction G by the force of the agent within cartridge 408B, and/or may be urged in direction G by other user actuation, as discussed with respect to FIG. 5B below. Although not shown, distal cover 462B may include a biasing element, for example, a spring connecting a portion of end flap 470 to arm 472. Alternatively or additionally, end flap 470 may be formed of a shape memory material. In this aspect, when the plunger (not shown) and/or cartridge 408B are stationary and some or all of the agent(s) has been delivered from cartridge 408B, distal cover 462B may help to close distal opening 438.

Figure 4C:
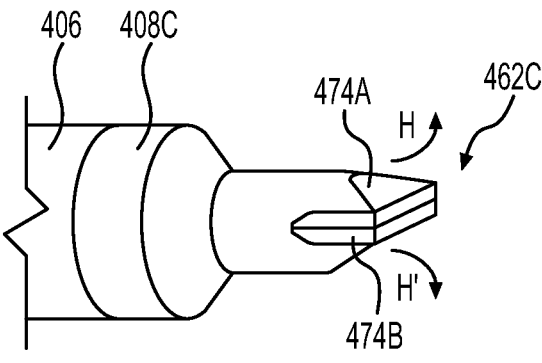

FIG. 4C shows shaft 406, cartridge 408C, and a third distal cover 462C. Third distal cover 462C may be a movable valve, for example, including two opposing valve arms 474A and 474B, which may cover and/or enclose distal opening 438 of cartridge 408C. Valve arms 474A and 474B may be expandable and/or pivotable, for example, in directions H and H', respectively, to at least partially expose distal opening (not shown), such that the one or more treatment agents in cartridge 408C may be delivered. Third distal cover 462C, including valve arms 474A and 474B, may be urged in directions H and H' by the force of the agent within cartridge 408C, and/or may be urged in directions H and H' by other user actuation, as discussed with respect to FIG. 5B below. Although not shown, valves arms 474A and 474B may include a biasing element, for example, a spring connecting portions of valve arms 474A and 474B. Alternatively or additionally, valve arms 474A and 474B may be formed of a shape memory material. In this aspect, when the plunger (not shown) and/or cartridge 408C are stationary and some or all of the agent has been delivered from cartridge 408C, valve arms 474A and 474B may help to close the distal opening (not shown).

Figure 4D:
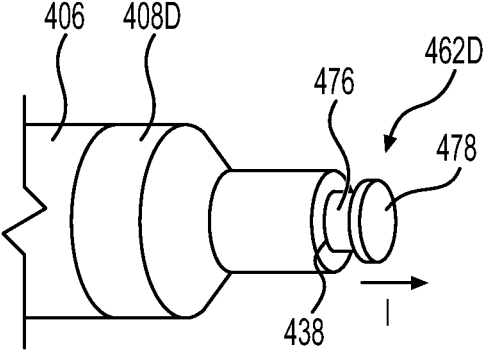

FIG. 4D shows shaft 406, cartridge 408D, and a fourth distal cover 462D. Fourth distal cover 462D may be a movable or puncturable element, for example, a plug, a film, a membrane, a frangible portion or segment, etc. Fourth distal cover 462D may be urged in direction I by the force of the agent within cartridge 408D. Additionally or alternatively, as discussed in detail with respect to FIG. 5B, the movable or puncturable element may be moved (e.g., pushed distally) or punctured, for example, via a portion or extension of the plunger and the relative movement of the plunger and the cartridge 408D. In this aspect, the movement or puncturing may expose at least a portion of distal opening 438. In one aspect, distal cover 462D be a plug, for example, including a proximal portion or cylindrical portion 476, for example, sized and configured to be received within a portion of distal opening 438. In some aspects, distal cover 462D may also include a widened portion 478, for example, at a distal portion of distal cover 462D and wider than cylindrical portion 476 and/or distal opening 438. As discussed with respect to FIG. 5B, distal cover 462D may be pushed or advanced distally (i.e., by the movement of the agent within cartridge 408D and/or by other user actuation), for example, in direction I, to at least partially expose distal opening 438, such that the one or more agents in cartridge 408D may be delivered. Although not shown, distal cover 462D may include a connection element, for example, a string connecting a portion of distal cover 462D to shaft 406 or cartridge 408D to help retain distal cover 462D in proximity to shaft 406 or cartridge 408D.

Figure 4E:
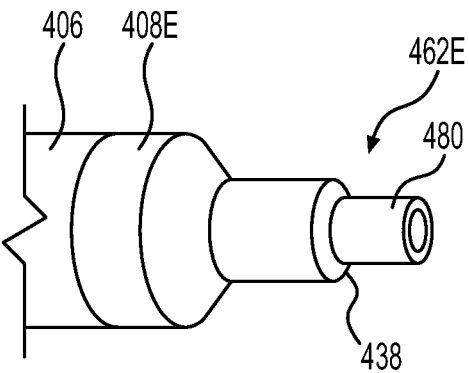

FIG. 4E shows shaft 406, cartridge 408E, and a fifth distal cover 462E. Fifth distal cover 462E may be a liner element 480. For example, liner element 480 may extend from distal opening 438. For example, liner element 480 may be positioned within a portion of the distal lumen (FIG. 3A) of cartridge 408E. Liner element 480 may also extend distally beyond the distal lumen and distal opening 438 of cartridge 408E. Liner element 480 may be hydrophobic and/or non-stick, for example, to help allow for the agent(s) to be delivered from cartridge 408E, while also helping to prevent the agent(s) from hardening and/or helping to prevent clogs forming. For example, liner element 480 may be generally cylindrical, and may be formed of Fluorinated ethylene propylene ("FEP"), Polytetrafluoroethylene ("PTFE"), or other appropriate material. In these aspects, when the plunger (not shown) and/or cartridge 408E are stationary and some or all of the treatment agent has been delivered from cartridge 408E, distal cover 462E may help to prevent a treatment agent within cartridge 408E from passing through distal opening 438 or otherwise being inadvertently dispersed or delivered, for example, by forming a resistive, narrow column. Moreover, distal cover 426E may help to maintain a patency of distal opening 438 or cartridge 408E, for example, by providing a hydrophobic and/or non-stick liner to distal opening 438 to help prevent the treatment agent (not shown) from adhering, solidifying, etc. to the internal walls at a distal portion of cartridge 408E, for example, distal opening 438.

Figures 5A, 5B:
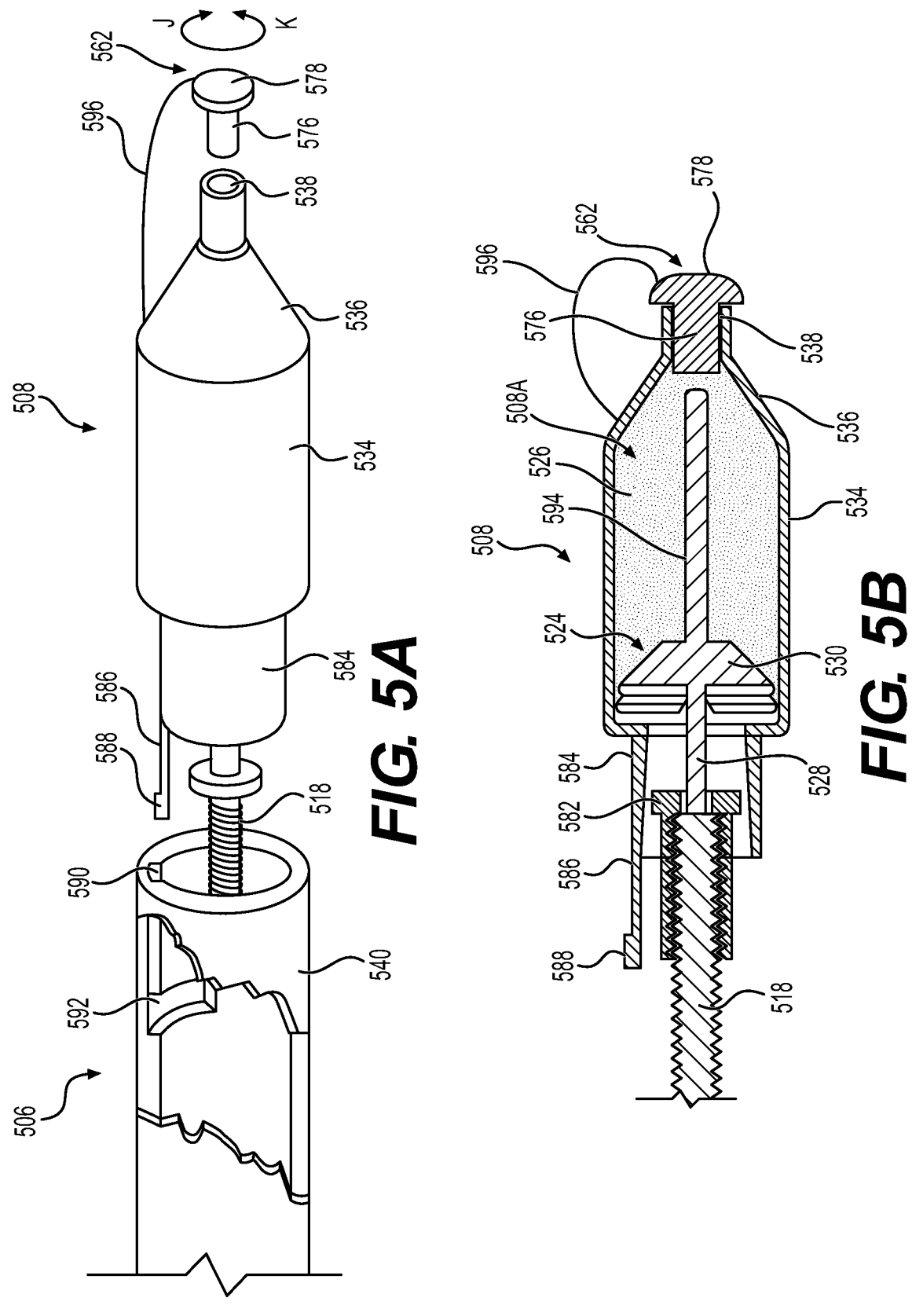
FIG. 5A is a partially exploded and cut-away view of a portion of another embodiment of the distal end of the insertion portion and an exemplary cartridge.
FIG. 5B is a cross-sectional view of the cartridge, according to aspects of this disclosure.

FIG. 5A is a partially exploded and cut-away view of a portion of the distal end of a shaft 506 and a cartridge 508, and FIG. 5B is a cross-sectional view of cartridge 508 and an actuation member 518, according to additional aspects of this disclosure. As shown in FIG. 5A, actuation member 518 may include a cable, for example, a Bowden cable. Alternatively, as discussed above, actuation member 518 may include a wire, a strand, a cord, a chain, a thread, etc. Actuation member 518 extends from the handle (not shown), and through at least a portion of shaft 506, for example, interior to a portion of an outer sheath 540. As shown in FIG. 5B, actuation member 518 may be coupled to a proximal portion 528 (e.g., a proximally extending rod) of a plunger 524, for example, via a coupler 582. For example, coupler 582 may be coupled to proximal portion 528 via an adhesive, a snap-fit, a press-fit, a crimp, or other coupling, etc., and coupler 582 may be coupled to a distal portion of actuation member 518 via an adhesive, a snap-fit, a press-fit, a crimp, or other coupling, etc. In this aspect, distal movement of actuation member 518, for example, via distal movement of actuator 110 (FIG. 1), may advance plunger 524 distally. Furthermore, distal movement of plunger 524 may push agent 526 out of cartridge 508, for example, out of a cartridge cavity 508A and through distal opening 538.

As discussed above with respect to FIGS. 3A-3C, in some aspects, although not shown, cartridge 508 may be removable from sheath 540 with plunger portion 524 (or a portion of plunger portion 524) remaining in and/or coupled to cartridge 508. For example, actuation member 518 may be selectively mated (i.e., coupled and uncoupled) to plunger portion 524. In this aspect, actuation member 518 may mate with plunger portion 524 when cartridge 508 is coupled to the distal portion of sheath 540, and actuation member 518 may disconnect from plunger portion 524 when cartridge 508 is uncoupled from the distal portion of sheath 540. Alternatively or additionally, plunger portion 524 may be a part of cartridge 508 (e.g., a non-removable part of cartridge 508). For example, a distal portion of actuation member 518 may abut a proximal portion of plunger portion 524 (e.g., proximal portion 528), such that distal movement of actuation member 518 may also distally advance plunger portion 524, without actuation member 518 and plunger portion 524 being solidly coupled or attached. In one aspect, a proximal end of proximal portion 528 may be received with an opening on a distal end of actuation member 518 and/or an opening on a distal end of coupler 582.

As shown in FIGS. 5A and 5B, cartridge 508 may be releasably coupled and/or locked or otherwise secured to a distal end of shaft 506. In this aspect, cartridge 508 may include a coupling portion 584, which may extend proximally from proximal portion 534 of cartridge 508 and, for example, at least partially overlap longitudinally with coupler 582. Additionally, cartridge 508 may include proximal extension 586. For example, proximal extension 586 may extend proximally from a portion of coupling portion 584 of cartridge 508. Additionally, proximal extension 586 may include a radial extension or peg 588, for example, with a greater radial thickness (i.e., relative to a longitudinal axis of cartridge 508) than proximal extension 586. A distal portion of shaft 506 may include a longitudinal slot 590, for example, extending longitudinally along an inner surface of sheath 540. Longitudinal slot 590 may connect to a radial slot 592, for example, extending radially along an inner circumferential surface of sheath 540 at a position proximal of the distal end of sheath 540. For example, radial slot 592 may extend perpendicular to a longitudinal axis of shaft 506, along approximately 180 degrees, approximately 90 degrees, approximately 75 degrees, approximately 60 degrees, approximately 45 degrees, etc. of the inner surface of sheath 540. Longitudinal slot 590 may be approximately the same longitudinal length as proximal extension 586. Additionally, radial slot 592 may include a width (e.g., measured parallel to the longitudinal axis of shaft 506) that is a similar to or greater than a longitudinal length of peg 588.

In these aspects, proximal extension 586 and peg 588 may be inserted proximally into longitudinal slot 590 to help couple cartridge 508 to shaft 506. Additionally, cartridge 508 may be rotated, for example, in a direction J, to rotate proximal extension 586 and peg 588, such that peg 588 is positioned within radial slot 592 to help couple cartridge 508 to shaft 506. In these aspects, the depth of longitudinal slot 590 and radial slot 592 may correspond to a depth (i.e., a radial width) of peg 588 relative to proximal extension 586. Additionally, when cartridge 508 is rotated such that peg 588 is positioned within radial slot 592, the remainder of proximal extension 586 may be positioned radially within and/or abut the inner surface of sheath 540. Furthermore, for example, after agent 526 within cartridge 508 is dispensed (as discussed below), cartridge 508 may be rotated, for example, in a direction K, to rotate proximal extension 586 and peg 588, such that peg 588 is aligned with longitudinal slot 590. Then, proximal extension 586 and peg 588 may be pulled distally along longitudinal slot 590 to help uncouple cartridge 508 to shaft 506. As mentioned, cartridge 508 may be uncoupled from shaft 506, for example, after the one or more agents 526 within cartridge 508 have been delivered, and such that another cartridge may be coupled to shaft 506 (e.g., to replace a used cartridge 508 with a new cartridge 508).

Additionally, as shown in FIGS. 5A and 5B, a plug 562 may be couplable to a distal end of cartridge 508, for example, to at least partially block distal opening 538. As discussed with respect to FIG. 4D, plug 562 may include a cylindrical portion 576, for example configured to extend within distal opening 538. Moreover, plug 562 may include a widened portion 578 at a distal end.

As shown in FIG. 5B, plunger 524 may include or be coupled to a rod 594, for example, extending distally of a distal portion 530 of plunger 524. In this aspect, distal movement of plunger 524 may advance rod 594, and rod 594 may contact plug 562 (e.g., a proximal end of cylindrical portion 576) and help to push plug 562 out of distal opening 538, such that agent 526 may be delivered from cartridge 508. In this aspect, as discussed with respect to FIGS. 1 and 2A, an actuator may be advanced distally within a slot on a handle to distally advance actuation member 518 and plunger 524. Alternatively, as discussed with respect to FIGS. 3A-3C, an actuator may be rotated relative to a portion of the handle to rotate actuation member 518. For example, a portion of shaft 506, sheath 540, or coupler 582 may provide for a threaded interaction such that rotation advances actuation member 518 and also advances plunger 524 and rod 594. In another aspects, as discussed with respect to FIGS. 2B and 2C, an actuator may be proximally retracted such that an actuation member is proximally retracted to either pull plunger 524 distally (e.g., by looping around a fulcrum element, as discussed with respect to FIG. 2B) or to pull cartridge 508 proximally (e.g., with the actuation member coupled to the cartridge, as discussed with respect to FIG. 2C). In any of these aspects, rod 594 may extend approximately 50%, approximately 60%, approximately 70%, approximately 80%, approximately 90%, or approximately 95% of a length of cartridge cavity 508A that contains agent 526. Additionally, rod 594 may have a cross-sectional size smaller (e.g., diameter) than the size of distal opening 538, for example, such that agent 526 may be delivered around rod 594 to the treatment site. Furthermore, it is noted that any of the embodiments discussed herein (i.e., FIGS. 1, 2A-2C, 3A-3C, and 4A-4E) may include a rod similar to rod 594 extending from distal portions of respective plunger, for example, to help open, expose, or otherwise clear the distal openings of the cartridges.

In one or more aspects, plug 562 may be coupled to a portion of cartridge 508 via a connecting element 596, for example, a wire, strand, string, tab, etc. Although not shown, alternatively or additionally, plug 562 may be coupled to a portion of shaft 506 via connecting element 596 or via another connecting element. In these aspects, when plug 562 is pushed out of distal opening 538 by rod 594, connecting element 596 may help to retain plug 562, such that plug 562 remains in the vicinity of cartridge 508, the distal portion of shaft 506, or otherwise at or near the treatment site. In these aspects, plug 562 may be removed when shaft 506 and cartridge 508 are removed from the treatment site. Alternatively, another treatment device (e.g., a grasper, basket, etc.) may be used to retrieve and collect plug 562, for example, by capturing plug 562 and/or separating plug 562 from connecting element 596. Alternatively or additionally, plug 562 may be formed of a biocompatible material that may safely dissolve or otherwise breakdown in the patient.

Figure 6:
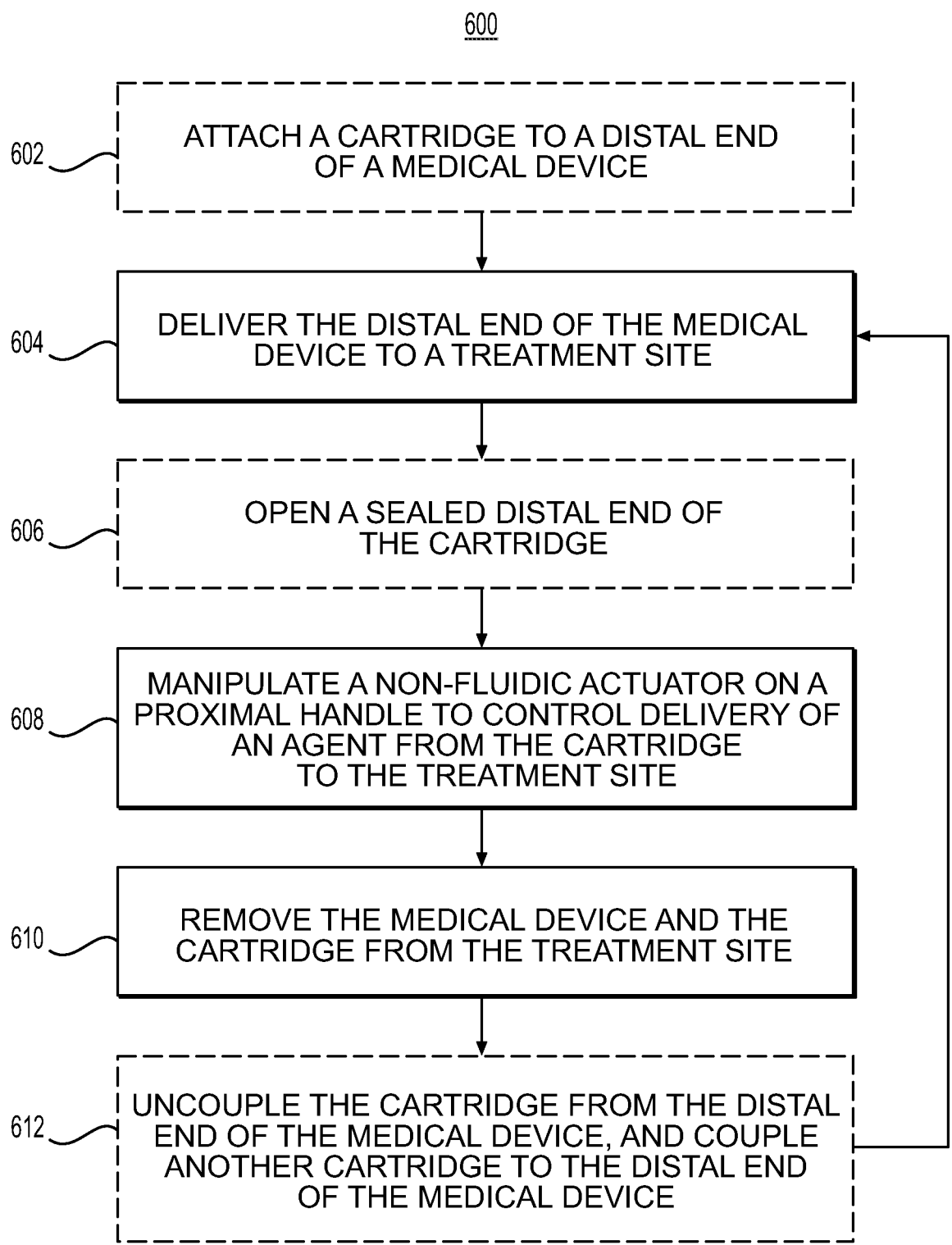
FIG. 6 is a flow diagram of an exemplary method, according to aspects of this disclosure.

FIG. 6 illustrates a method 600 that may be performed with any of medical systems or portions of systems discussed herein. An optional first step 602 includes attaching a cartridge 108, 208, 208', 308, 408A-E, 508 to a distal end of a medical device 102, for example, to a distal end of shaft 106, 306, 406, 506. As discussed with respect to FIGS. 2A-2C, the cartridge may abut a distal end of the shaft, or may be at least partially received within the distal end of the shaft. As discussed with respect to FIG. 3A, the distal end of the shaft may include one or more shapes, contours, etc. to help retain the cartridge. Furthermore, as discussed with respect to FIGS. 5A and 5B, cartridge 508 may be releasably coupled to distal end of shaft 506, for example, to a distal end of sheath 540.

Next, a step 604 includes delivering the distal end of the medical device to a treatment site. As discussed above, the distal end of the medical device may be delivered to the treatment site via an insertion device, for example, though a lumen of the insertion device or adjacent to or along an outer wall of the insertion device (i.e., in a "side-saddle" arrangement). Alternatively, the distal end of the medical device may be delivered to the treatment site directly, for example, via a guide wire, steering, imaging, etc.

Next, an optional step 606 includes opening a sealed distal end of the cartridge. The sealed distal end of the cartridge may help to prevent contamination during the delivery to the treatment site and/or may help to prevent curing of the one or more agents within the cartridge. As discussed with respect to FIGS. 4A-4E and 5A-5B, one of the distal covers may be coupled to a distal end of the cartridge. The distal cover may be reclosable, for example, as discussed with respect to FIGS. 4A-4C and 4E. Alternatively, the distal cover may be removable via action on a proximal actuator, for example, as discussed with respect to FIGS. 4D, 5A, and 5B.

A step 608 includes manipulating an actuator on a proximal handle to deliver an agent from the cartridge to the treatment site. As discussed with respect to FIGS. 1, 2A, 5A, and 5B, the manipulation of the actuator may include distally advancing the actuator to deliver the agent. Alternatively, as discussed with respect to FIGS. 2B and 2C, the manipulation of the actuator may include proximally retracting the actuator to deliver the agent. Furthermore, as discussed with respect to FIGS. 3A-3C, the manipulation of the actuator may include rotating the actuator to deliver the agent. In any of these aspects, the agent may be incrementally and/or controllably delivered from cartridge out of the distal end of the cartridge. Furthermore, the actuation may be non-fluidic, for example, such that the proximal manipulation of the actuator delivers a non-fluidic force on a portion of a plunger or the cartridge to deliver the agent out of the cartridge. Additionally, as mentioned, the agent may include one or more agents. Moreover, in some aspects, as discussed with respect to FIG. 1, handle 104 may include a plurality of indications or markings 114, for example, numbers or other indications or markings adjacent to actuator 110 within slot 112. The indications or markings 114 may help the user correlate the position of actuator 110 within slot 112 to an amount of the one or more agents remaining in cartridge 108 and/or and amount of the one or more agents delivered to the treatment site to a position of actuator 110.

Then, a step 610 includes removing the medical device and the cartridge from the treatment site. Step 610 may include removing the medical device and the cartridge from the treatment site through or along the insertion device. Alternatively, step 610 may include removing the medical device and the cartridge separately from the insertion device, for example, if the medical device and the cartridge were not delivered via an insertion device. As mentioned with respect to FIGS. 5A and 5B, this step may also include removing plug 562, for example, which may be connected to cartridge 508 or a distal end of shaft 506 via connecting element 596.

Furthermore, an optional step 612 includes uncoupling the cartridge from the distal end of the medical device, and coupling another cartridge to the distal end of the medical device. As discussed with respect to FIGS. 5A and 5B, cartridge 508 may be releasably coupled to the distal end of the shaft 506, for example, to the distal end of the sheath 540 via the interaction of proximal extension 586 and peg 588 with longitudinal slot 590 and radial slot 592. In this aspect, if the contents (i.e., agent(s) 526) within a first cartridge have been delivered to the treatment site, then the first cartridge may be separated from the distal end of the shaft. Furthermore, a second cartridge with additional or different agent(s) may then be coupled to the distal end of the shaft for additional treatment of the treatment site. Lastly, if additional treatment (i.e., the delivery of additional agent(s)) is needed at the treatment site, then method 600 may return to step 604.

The systems, devices, and methods discussed herein may allow for one or more agents (e.g., liquid or fluidic agents) to be delivered to a treatment site. Additionally, in some aspects, the delivery of the one or more agents is controlled via a non-fluidic actuation. For example, movement of the one or more actuation member (e.g., via movement of the actuator on the handle) may control the delivery of the fluidic agent from the cartridge. In these aspects, there may be a reduced likelihood of the fluidic agent curing, solidifying before being delivered to the treatment site, causing one more clogs in the medical device or cartridge, etc. Additionally, the movement of the actuation member may control the movement of the plunger, which may help to allow for the one or more agents to be delivered in a controlled manner, such that a desired amount of the one or more agents may be delivered to the treatment site. Furthermore, the handle may include one or more indications or markings, which may help the user correlate a position of the actuator to an amount of the one or more agents remaining in the cartridge and/or delivered to the treatment site. In some aspects, the cartridge may also be removably coupled to the distal end of the shaft, for example, such that multiple cartridges may be coupled to the distal end of the shaft in order to replace a user cartridge, deliver a different agent(s) to the treatment site, etc. Various aspects discussed herein may help facilitate and/or improve the efficacy, efficiency, cost, and/or safety of a medical procedure.

Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

It should be understood that one or more of the aspects of any of the medical systems, devices, and methods described herein may be using in combination with any other medical system, device, or method known in the art, such as medical imaging systems, catheters, elongate instruments, or other scopes such as colonoscopes, bronchoscopes, ureteroscopes, duodenoscopes, etc., or other types of imagers. It also should also be understood that one or more aspects of any of the medical systems, devices, and methods described herein may be used for treating tissue in any part of the human body. For example any of the medical systems, devices, and methods described herein may be used in medical procedures such as for endoscopic cholangio-pancreatography, colonoscopies, cancer screening, examination of mucinous lesions, and/or other procedures where removal and/or detection of the type of tissue is needed.

While principles of the present disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:
1. A medical system, comprising:
a medical device having a handle, a shaft, and an actuation member including a plurality of wires, wherein the handle includes an actuator movable relative to the handle, and wherein the actuator is coupled to a distal end of the shaft via the actuation member;
a cartridge containing a treatment agent, wherein the cartridge is couplable to the distal end of the shaft; and
a plunger that is movable relative to the cartridge,
wherein the distal end of the shaft includes a plurality of fulcrum portions fixed within the distal end of the shaft, wherein each of the plurality of wires is paired with one of the plurality of fulcrum portions, and wherein each of the plurality of wires extends from the actuator distally beyond each of the plurality of fulcrum portions to a portion of the plunger proximate to the plurality of fulcrum portions, such that proximal movement of the actuator urges the plurality of wires proximally and also urges the plunger distally to deliver the treatment agent from the cartridge.

2. The medical system of claim 1, wherein the treatment agent is an adhesive.

3. The medical system of claim 2, wherein the treatment agent is a cyanoacrylate.

4. The medical system of claim 1, wherein each of the plurality of fulcrum portions include a ring fixed within an internal portion of the distal end of the shaft.

5. The medical system of claim 1, wherein the cartridge is removably coupled to the distal end of the shaft.

6. The medical system of claim 5, wherein the cartridge includes a proximal extension with a peg, wherein the distal end of the shaft includes a slot, and wherein positioning the proximal extension within the slot removably couples the cartridge to the distal end of the shaft.

7. The medical system of claim 6, wherein the slot includes a longitudinal slot and a radial slot, wherein the radial slot extends along a portion of an inner circumferential surface of the shaft in a direction perpendicular to a longitudinal axis of the shaft.

8. The medical system of claim 1, wherein the handle includes a plurality of markings indicative of an amount of the treatment agent that has been delivered and/or remains within the cartridge.

9. The medical system of claim 1, wherein the cartridge includes a distal cover that is either openable or removable to expose a distal opening of the cartridge and to allow the treatment agent to be delivered from the distal opening.

10. The medical system of claim 9, wherein the distal cover is a plug, and wherein the plug is coupled to the cartridge via a connecting element.

11. The medical system of claim 1, further comprising a liner element, wherein the liner element is coupled to a distal end of the cartridge, and wherein the liner element is hydrophobic and/or non-stick.

12. The medical system of claim 1, wherein the actuation member further comprises a split proximate to the plunger, wherein, at the split, each of the plurality of wires extends distally towards each of the paired fulcrum portions.

13. A medical device, comprising:
an actuation member;
a cartridge containing a treatment agent, wherein the cartridge includes a proximal extension with a peg, and wherein the cartridge is removably couplable to a distal end of a shaft via the proximal extension; and
a plunger that is movable relative to the cartridge,
wherein the distal end of the shaft includes a plurality of fixation portions extending radially inwards within the shaft, wherein a first portion of the actuation member extends around a first fixation portion of the plurality of fixation portions to a first portion of the plunger proximate to the first fixation portion, wherein a second portion of the actuation member extends around a second fixation portion of the plurality of fixation portions to a second portion of the plunger proximate to the second fixation portion, and wherein proximal movement of the actuation member urges the first portion of the actuation member and the second portion of the actuation member proximally and also urges the plunger distally to deliver the treatment agent from the cartridge.

14. The medical device of claim 13, wherein the treatment agent is a cyanoacrylate.

15. The medical device of claim 13, wherein the cartridge includes a distal cover that is removable or openable to expose a distal opening of the cartridge and to allow the treatment agent to be delivered from the distal opening.

16. The medical device of claim 13, wherein the actuation member further comprises a split proximate to the plunger, wherein, at the split, the first portion of the actuation member and the second portion of the actuation member extend distally towards the first fixation portion and the second fixation portion respectively.

17. The medical device of claim 13, wherein at least one of the first fixation portion or the second fixation portion are one of: a partially circular element or a ring.

18. A method, comprising:
delivering a distal end of a medical device to a treatment site;
manipulating an actuator on a proximal handle to deliver an agent from a cartridge to the treatment site, wherein the actuator actuates a plurality of actuation members, wherein each of the plurality of actuation members is paired with a portion of a fulcrum element, wherein proximal movement of the actuator urges a plunger distally to deliver the agent from the cartridge; and
removing the medical device and the cartridge from the treatment site.

19. The method of claim 18, further comprising:
attaching the cartridge to the distal end of the medical device;
before manipulating the actuator on the proximal handle to deliver the agent from the cartridge to the treatment site, opening or exposing a sealed distal end of the cartridge; and
after removing the medical device and the cartridge from the treatment site, uncoupling the cartridge from the distal end of the medical device, and coupling another cartridge to the distal end of the medical device.

20. The method of claim 18, wherein the agent is an adhesive or a cyanoacrylate.

* * * * *